(12) United States Patent
Littlefield

(10) Patent No.: US 10,166,716 B2
(45) Date of Patent: *Jan. 1, 2019

(54) METHOD OF MANUFACTURING A MEDICAL DEVICE FOR EXTERNAL APPLICATION TO THE HEAD OF A PATIENT

(71) Applicant: CRANIAL TECHNOLOGIES, INC., Tempe, AZ (US)

(72) Inventor: Timothy R Littlefield, Phoenix, AZ (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/982,200

(22) Filed: May 17, 2018

(65) Prior Publication Data

US 2018/0264714 A1    Sep. 20, 2018

Related U.S. Application Data

(62) Division of application No. 14/588,282, filed on Dec. 31, 2014, now Pat. No. 9,987,801.

(51) Int. Cl.

| | |
|---|---|
| *B29C 67/00* | (2017.01) |
| *B29C 64/10* | (2017.01) |
| *B29C 64/188* | (2017.01) |
| *B29C 64/386* | (2017.01) |
| *A61F 2/50* | (2006.01) |
| *B29K 69/00* | (2006.01) |
| *B29L 31/00* | (2006.01) |
| *B33Y 10/00* | (2015.01) |
| *B33Y 50/02* | (2015.01) |
| *B33Y 80/00* | (2015.01) |

(52) U.S. Cl.
CPC ............ *B29C 64/10* (2017.08); *B29C 64/188* (2017.08); *B29C 64/386* (2017.08); *A61F 2002/5049* (2013.01); *B29K 2069/00* (2013.01); *B29K 2995/0026* (2013.01); *B29L 2031/7532* (2013.01); *B33Y 10/00* (2014.12); *B33Y 50/02* (2014.12); *B33Y 80/00* (2014.12)

(58) Field of Classification Search
CPC ................. B29C 64/188; B29C 64/386; B29L 2031/7532

See application file for complete search history.

(56) References Cited

U.S. PATENT DOCUMENTS

| | | | | |
|---|---|---|---|---|
| 5,156,777 | A * | 10/1992 | Kaye ..................... | A61F 2/2803 264/222 |
| 6,932,610 | B2 * | 8/2005 | Ono ....................... | A61L 27/443 434/267 |
| 7,050,877 | B2 * | 5/2006 | Iseki ..................... | A61F 2/2875 623/17.19 |

(Continued)

*Primary Examiner* — Atul P. Khare

(74) *Attorney, Agent, or Firm* — Donald J Lenkszus

(57) ABSTRACT

A method of manufacturing a custom device for external application to the head of a patient over a removed portion of the cranium of the patient is described. A three dimensional digital image portion of the external surface of the head comprising at least the removed portion is generated. A three dimensional digital image portion is processed to identify the removed portion. A digital file is generated that is utilized to manufacture the device.

17 Claims, 12 Drawing Sheets

(56) References Cited

U.S. PATENT DOCUMENTS

| | | | |
|---|---|---|---|
| 7,747,305 B2* | 6/2010 | Dean | A61F 2/30942 600/407 |
| 7,935,858 B2* | 5/2011 | Praetzel | A61F 13/00068 128/888 |
| 8,103,088 B2* | 1/2012 | Luisi | A61B 5/0077 348/48 |
| 8,142,886 B2* | 3/2012 | Noble | A61F 2/2875 264/497 |
| 8,862,258 B2* | 10/2014 | Nimal | A61L 27/12 700/98 |
| 8,974,535 B2* | 3/2015 | Antonyshyn | A61F 2/2875 623/17.18 |
| 9,468,502 B2* | 10/2016 | Wiebe, III | A61B 17/1764 |
| 2004/0179728 A1* | 9/2004 | Littlefield | G06T 1/0007 382/154 |
| 2015/0170416 A1* | 6/2015 | McGregor | G06T 19/20 345/420 |
| 2015/0173815 A1* | 6/2015 | Breault | A61B 17/8061 606/286 |
| 2016/0346091 A1* | 12/2016 | Bin Abdul Rahman | A61F 2/2875 |
| 2017/0224494 A1* | 8/2017 | Li | A61F 2/30942 |

\* cited by examiner

METHOD OF MANUFACTURING A MEDICAL DEVICE FOR EXTERNAL APPLICATION TO THE HEAD OF A PATIENT

RELATED APPLICATIONS

This application is a division of copending U.S. patent application Ser. No. 14/588,282, filed Dec. 31, 2014.

FIELD OF THE INVENTION

The present invention relates to methods for manufacture of medical devices, in general, and to a method for manufacture of medical devices for external application to the head of a patient, in particular.

BACKGROUND

Many medical conditions related to the head of a patient may be treated by the use of medical devices that are externally applied to the head of the patient.

One set of medical conditions, e.g., trauma, tumor, disease, are known to cause the brain to swell, increasing intracranial pressure (ICP). In many situations this increase in ICP may be life threatening, requiring a surgical procedure known as a decompressive craniotomy. In this procedure, a large segment of cranial bone, known as the bone flap, is removed from the cranium. The removal of the bone flap relieves the intracranial pressure by allowing the brain to temporarily swell through the hole made in the cranium.

The bone flap is stored, with the intent of returning it to the cranium, once the swelling has subsided and the patient has stabilized, typically 4-6 weeks after the procedure. The bone flap is stored either by surgically inserting it into the abdomen, or by freezing it. Until the bone flap is replaced, it may be desirable to protect the portion of the head comprising the portion where the bone flap has been removed.

One option is to provide a external plate that is affixed to the scalp of the patient as described in a copending patent application Serial No. filed on even date herewith and assigned to a common assignee. The contents of that application are incorporated herein by reference.

Accordingly, it is desirable to provide a method of manufacturing a medical device for external application to the head of a subject.

SUMMARY

In accordance with the principles of the invention, a plurality of stereographic digital image pairs of at least a portion of a head that is of interest is captured. The image pairs are processed to generate a three dimensional digital image and data file of at least of the portion of interest. The data file is utilized a device for affixation to the head of a patient.

One embodiment of a method of manufacturing a custom device for external application to the head of a patient over a removed portion of the cranium of the patient, comprises: generating a three dimensional digital image portion of the external surface of the head comprising at least the removed portion; processing the three dimensional digital image portion to identify the removed portion as a three dimensional removed portion digital image file; and processing the three dimensional removed portion digital image file to determine one or more of a size, shape, contour and alignment for the custom device and to generate a device data file.

An embodiment of a method of manufacturing a device for external application to the scalp of a patient over a removed portion of the cranium of the patient, comprises: providing a three dimensional digital image portion of the head of the patient comprising at least a portion of the head comprising the removed portion; processing the three dimensional digital image portion to identify at least the removed portion as a three dimensional removed portion image file; processing the three dimensional removed portion image file to determine one or more of a size, shape, contour and alignment for the cranial plate; and generating a device file from the processing step.

One embodiment of a method of manufacturing a cranial plate for external application to the scalp of a patient over a removed portion of the cranium of the patient, comprising: providing a three dimensional digital image portion of the head of the patient comprising at least a portion of the head comprising the removed portion; processing the three dimensional digital image portion to identify at least the removed portion; generating a shape for the cranial plate from the three dimensional digital image portion such that the cranial plate comprises a convex portion and extends over the scalp for a predetermined distance beyond the removed portion; and utilizing the shape to generate a data file utilizable to manufacture the cranial plate.

Another embodiment of a method of manufacturing a cranial plate for external application to the scalp of a patient over a removed portion of the cranium of the patient, comprises: providing a three dimensional digital image portion of the head of the patient comprising at least a portion the removed portion; processing the three dimensional removed portion image file to determine one or more of a size, shape, contour and alignment for the cranial plate; generating a cranial plate data file from the processing step; and utilizing the cranial plate data file to produce the cranial plate by one of an additive machining process, a subtractive machining process, and a combination of additive machining and subtractive machining.

An embodiment of a method of manufacturing a custom device for external application to the head of a subject, comprises: providing apparatus to capture a plurality of digital images of a plurality of portions of the external surface of the head; and processing the plurality of digital images to generate a three dimensional digital image and data file of at least a portion of the head comprising an area of the surface of the head to which the custom device is to be applied; and utilizing the data file to fabricate the custom device.

An embodiment of a method of manufacturing a device for external application to the head of a subject, comprises: providing stereographic digital camera apparatus to capture stereographic digital image pairs; utilizing the stereographic digital camera apparatus to capture a plurality of stereographic digital image pairs of a plurality of portions of the surface of the head; and processing the plurality of stereographic digital image pairs to generate a three dimensional digital image and a data file of at least a portion of the head comprising an area of the surface of the head to which the custom device is to be applied.

An embodiment of a method of manufacturing a custom cranial plate for external application to the scalp of a patient over a removed portion of the cranium of the patient, comprises: providing apparatus comprising a plurality of image capturing devices each arranged to capture a corresponding image of a corresponding surface portion of the head; simultaneously operating the plurality of image capturing devices to simultaneously capture a plurality of images of the head; processing the plurality of images to produce a three dimensional digital image of the head; identifying the removed portion on the three dimensional digital image of the head; selecting a three dimensional digital image portion extending over the scalp for a predetermined distance beyond the removed portion; and utilizing the selected three dimensional digital image portion to generate a data file utilizable to manufacture the custom cranial plate.

Another embodiment of a method of manufacturing a custom cranial plate for external application to the scalp of a patient over a removed portion of the cranium of the patient, comprises: providing a plurality of stereographic digital cameras each operable to capture a corresponding pair of stereographic images; positioning the plurality of stereographic digital cameras to simultaneously capture a corresponding plurality of stereographic digital image pairs of at least a corresponding vertical hemispherical portion of the head when the patient is positioned in a predetermined location with respect to the plurality of stereographic digital cameras; simultaneously operating the plurality of stereographic digital cameras to simultaneously capture a plurality of stereographic digital image pairs of the head; processing the plurality of stereographic digital image pairs to produce a three dimensional digital image of the head; identifying the removed portion on the three dimensional digital image of the head; selecting a three dimensional digital image portion extending over the scalp for a predetermined distance beyond the removed portion; and utilizing the selected three dimensional digital image portion to generate a data file utilizable to manufacture the custom cranial plate.

An embodiment of a method of manufacturing a custom cranial plate for external application to the scalp of a patient over a removed portion of the cranium of the patient, comprises: providing a stereographic digital camera operable to capture a corresponding pair of stereographic images; positioning the stereographic digital camera at a plurality of locations relative to the head to capture a plurality of stereographic digital image pairs of the head; operating the plurality of stereographic digital cameras in each of the positions to capture a plurality of stereographic digital image pairs of at least that portion of the head comprising the removed portion; processing the plurality of stereographic digital image pairs to produce a three dimensional digital image of the at least that portion of the head comprising the removed portion; selecting a three dimensional digital image portion extending over the scalp for a predetermined distance beyond the removed portion; and utilizing the selected three dimensional digital image portion to generate a data file utilizable to manufacture the custom cranial plate.

Another embodiment of a method of manufacturing a cranial plate for external application to the scalp of a patient over a removed portion of the cranium of the patient, comprises: providing a three dimensional digital image portion of the head of the patient comprising at least a portion of the head comprising the removed portion; processing the three dimensional digital image portion to identify the removed portion as a three dimensional removed portion image file processing the three dimensional removed portion image file to determine one or more of a size, shape, contour and alignment for the cranial plate; generating a cranial plate data file from the processing step; and utilizing the cranial plate data file to produce at least a portion of the cranial plate by thermoplastic forming.

An embodiment of a method for use with a subject having a removed cranium portion, comprises: providing a three dimensional digital image portion of the head of the subject comprising the removed portion, the three dimensional digital image portion produced from a plurality of digital images produced by one of a stereographic digital image camera, a plurality of stereographic digital image cameras, and a plurality of pairs of digital image cameras; and processing the three dimensional digital image portion to determine one or more of an initial cranial volume loss for the patient and a volume filling secondary to application of a cranial plate device fitted to the patient.

BRIEF DESCRIPTION OF THE DRAWING

The invention will be better understood from a reading of the following detailed description in conjunction with the drawing figures in which like reference designators are utilized to identify like element, and in which.

DETAILED DESCRIPTION

U.S. Pat. No. 7,127,101 issued Oct. 24, 2006; U.S. Pat. No. 7,142,701 issued Nov. 28, 2006; U.S. Pat. No. 7,162,075 issued Jan. 9, 2007; U.S. Pat. No. 7,177,461 issued Feb. 13, 2007; U.S. Pat. No. 7,227,979 issued Jun. 5, 2007; U.S. Pat. No. 7,242,798 issued Jul. 10, 2007; U.S. Pat. No. 7,245,743 issued Jul. 17, 2007; U.S. Pat. No. 7,280,682 issued Oct. 9, 2007; U.S. Pat. No. 7,305,369 issued Dec. 4, 2007; U.S. Pat. No. 7,542,950 issued Jun. 2, 2009; U.S. Pat. No. 8,103,088 issued Jan. 24, 2012; U.S. Pat. No. 8,217,993 issued Jul. 10, 2012; U.S. Pat. No. 8,442,288 issued May 14, 2013; U.S. Pat. No. 8,442,308 issued May 14, 2013; U.S. Pat. No. 8,472,681 issued Jun. 25, 2013; and U.S. Pat. No. 8,494,237 issued Jul. 23, 2013 are all assigned to the assignee of the present application and the disclosures contained in each of the patents are expressly incorporated herein by reference.

As used herein a "stereographic" or "three-dimensional" digital camera is used to describe a digital camera that is configured to acquire a plurality of two-dimensional digital images with identical magnification of a scene at different vantage points without relocating the camera to different locations. The stereographic digital camera may simultaneously or sequentially at a high rate of speed record each of a plurality of two-dimensional digital images. Various stereographic digital cameras are known in the prior art as are three-dimensional lens attachments to digital cameras that convert the two-dimensional digital camera into a stereographic digital camera. In one specific embodiment of the invention a conventional single lens reflex (SLR) digital camera is utilized with removable lens capability provided with a 3D lens, referred to by some suppliers as a "stereo lens". In that embodiment, the digital camera captures two two-dimensional images simultaneously.

After capturing the plurality of two-dimensional images, the stereographic digital camera may either store the resulting digital images onto a memory card or it may transmit the digital images to a processor either via cabling or via a wireless link or via a combination of one or more wireless links and a wired or cable link.

In certain embodiments, the processor and display are located in proximity to the stereographic digital camera. However, in other embodiments, either the processor or the processor and the display are remotely located from the stereographic digital camera.

As used herein, the term "stereographic digital images" refers to a pair of digital images captured simultaneously or sequentially at a high rate of speed, with each digital image being captured from a different vantage or view point.

Figure 1:
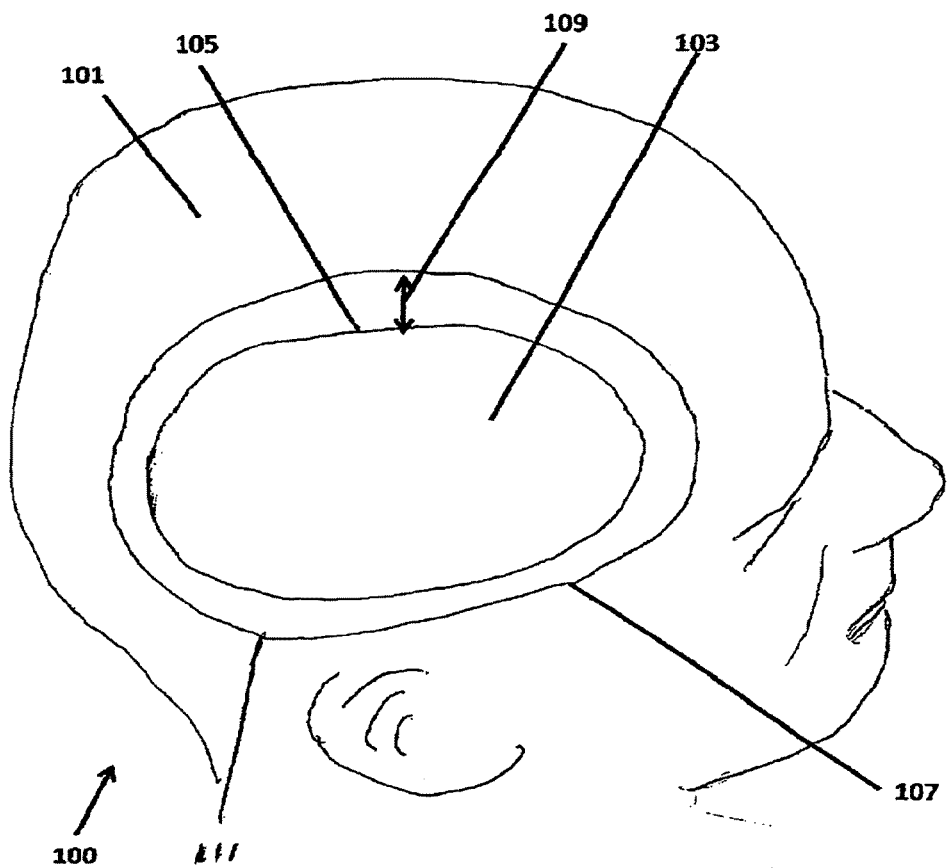
FIG. 1 is a model of a cranium with a removed portion.

Turning now to FIG. 1, a model 100 is shown of a head. Model 100 simulates the head of a patient that has had a decompressive craniotomy. The outer surface 101 of model 100 represents the scalp or skin covering the head. Model 100 includes a concave portion 103 that is representative of the depression that results as a result of a decompressive craniotomy in which a bone flap is removed. Concave portion 103 is bounded by edge 105. Edge 105 is representative of where the scalp covers the edge of the cranial bone. Line 107, which completely encircles concave portion 103, represents the perimeter of a custom manufactured external plate 200 shown in FIG. 2. Line 107 is spaced outward from concave portion 103 by a distance 109 forming a circumferential or peripheral scalp portion 111 that surrounds concave portion 103.

Figure 2:
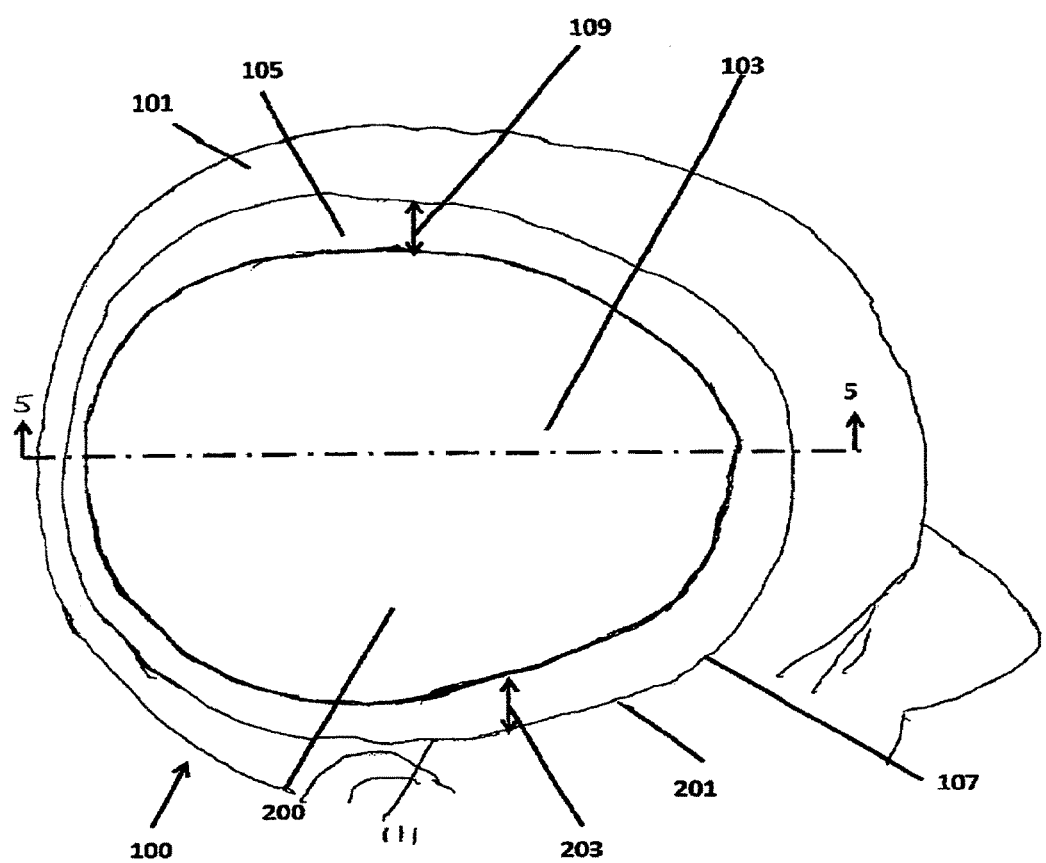
FIG. 2 shows the model of FIG. 1 with a external cranial plate.

In FIG. 2, external cranial plate 200 is in place on model 100. External cranial plate 200 is comprises a hard material. In the embodiment shown, cranial plate 200 comprises a polycarbonate material that is optically transparent thereby permitting observation of concave portion 103. external cranial plate 200 fully covers concave portion 103 and extends beyond edge 105 to line 107 along its entire periphery 201 providing a peripheral edge portion 203.

A bio-adhesive is utilized to removably affix peripheral edge portion 203 to the scalp in peripheral scalp portion 111. The bio-adhesive is applied along the entire peripheral edge portion 203. By utilizing a bio-adhesive, external cranial plate 200 is sealed in airtight and watertight engagement to peripheral scalp portion 111 covering the bone flap region or concave portion 103. The bio-adhesive utilized is one of a type commonly used with osteotomy products and can be used on skin for years with excellent tolerance.

Figure 3:
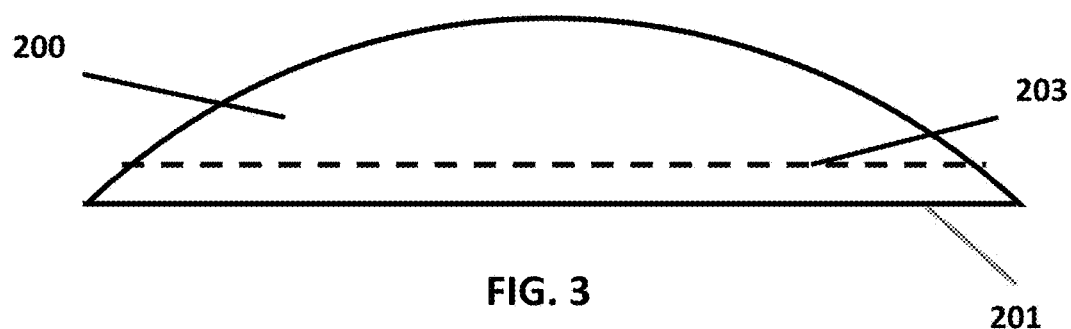
FIG. 3 is a top view of an embodiment of a external cranial plate.
Figure 4:
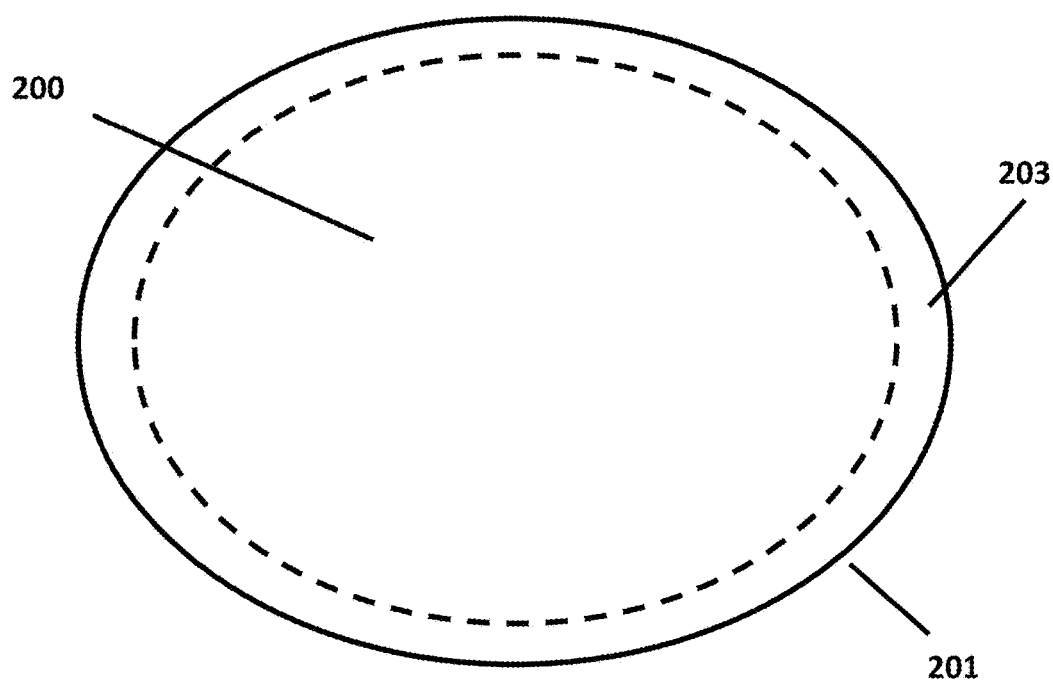
FIG. 4 is a side view of the embodiment of FIG. 3.
Figure 5:
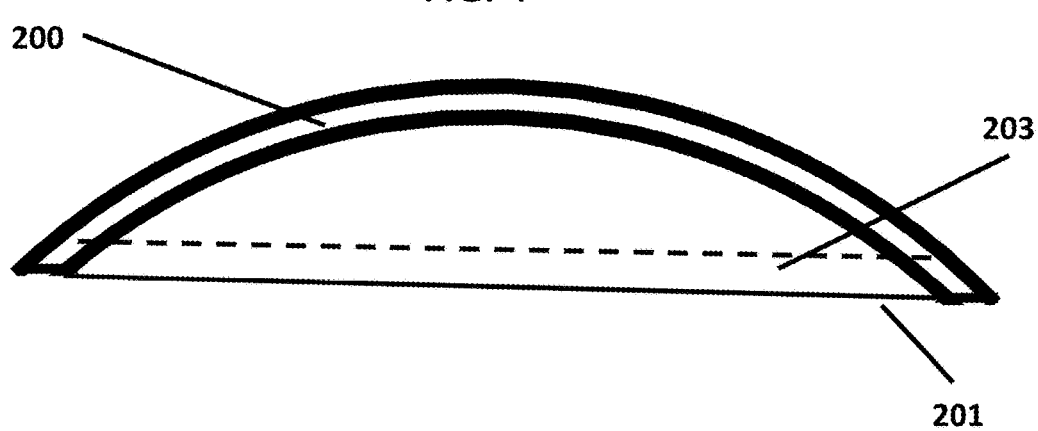
FIG. 5 is a cross-section of the embodiment of FIG. 3 taken along line 5-5.

FIGS. 3, 4 and 5 show an embodiment of external cranial plate 200. The side view in FIG. 3 and cross-section view of FIG. 5 clearly show that external cranial plate 200 is generally convex and its peripheral edge portion 203 is shaped to mate with the peripheral scalp portion 111.

Figure 6:
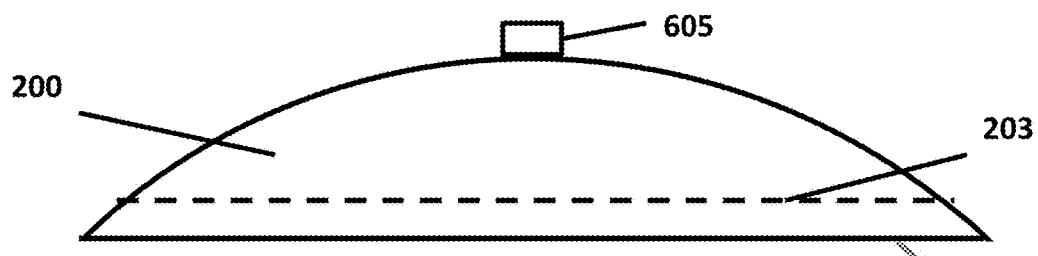
FIG. 6 is a top view of a second embodiment of a external cranial plate.
Figure 7:
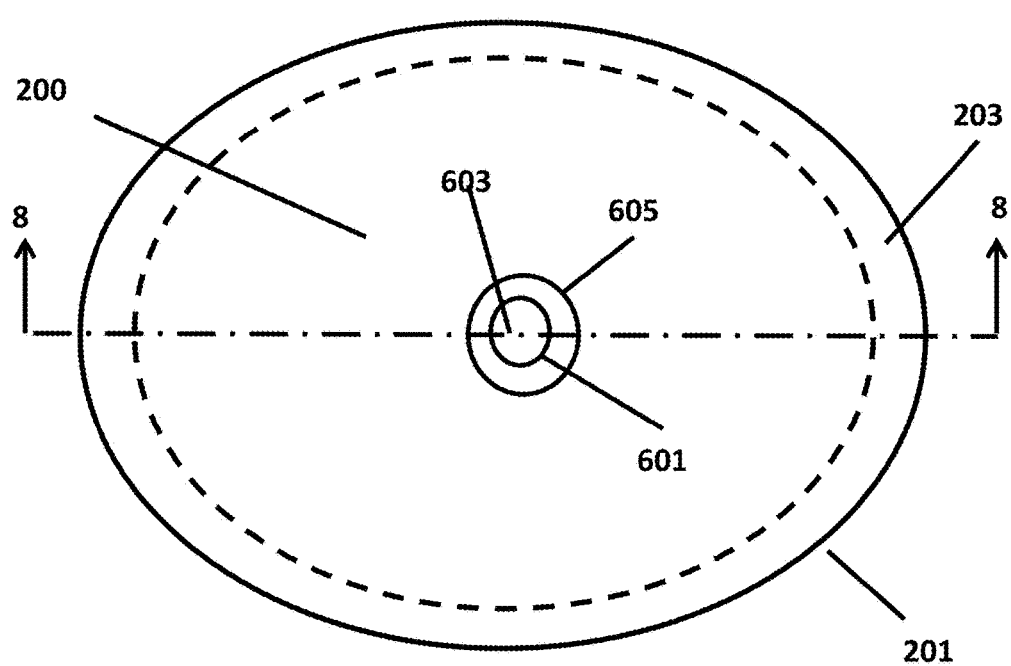
FIG. 7 is a side view of the embodiment of FIG. 6.
Figure 8:
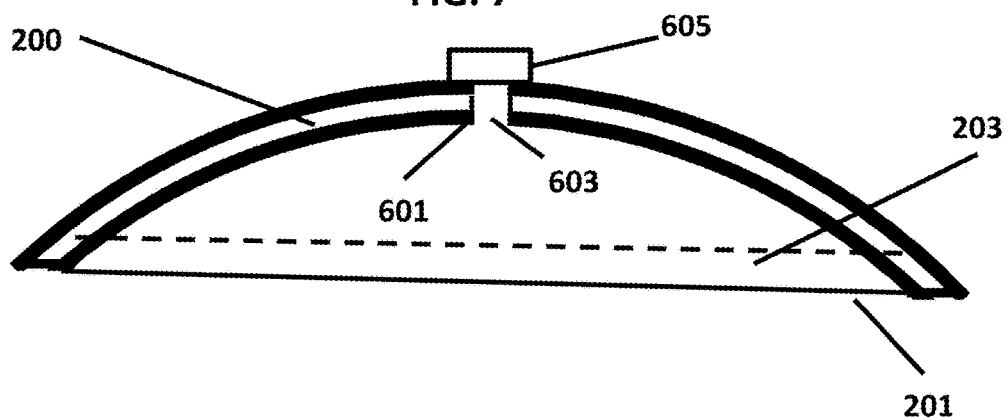
FIG. 8 is a cross-section of the embodiment of FIG. 6 taken along line 8-8 of FIG. 7

Another embodiment of a external cranial plate 600 is shown in FIGS. 6, 7, and 8. external cranial plate 600 has at least one port 601 formed therein. Port 601 comprises a through aperture 603. Through aperture 603 may have a valve 605 coupled therein. Valve 605 may be utilized to reduce the pressure under external cranial plate 200. Reducing the pressure under external cranial plate 200 to less than atmospheric pressure helps adhere external cranial plate 200 to the scalp. In addition reducing the pressure helps prevent cranial collapse and may also allow for rehydration of the brain.

Port 601 may also have a transducer or sensor carried therein. The transducer or sensor may be any transducer or sensor of medical interest such as, e.g., a pressure sensor or humidity sensor.

Figure 9:
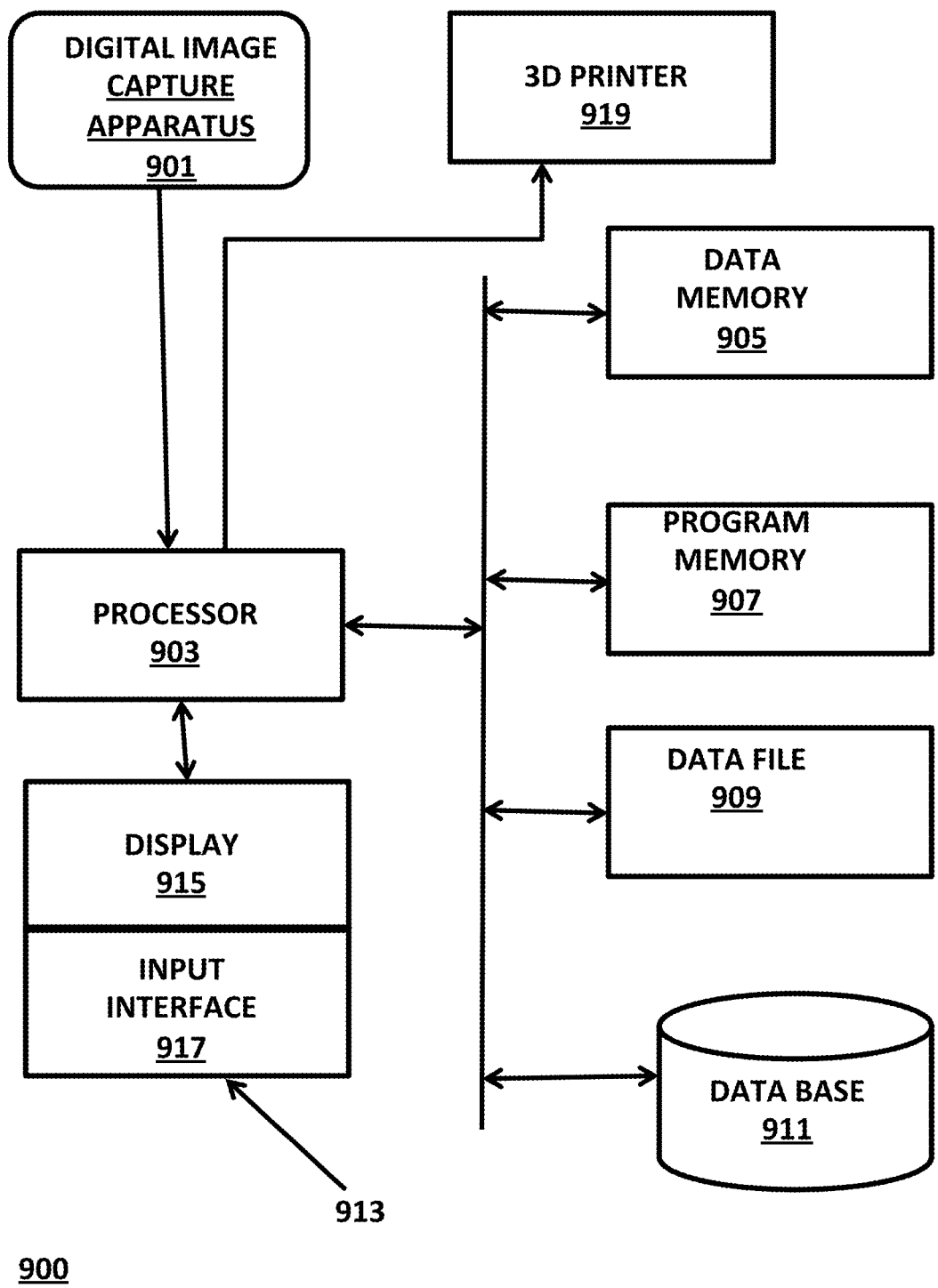
FIG. 9 is a block diagram of a system.

Turning now to FIG. 9, system 900 is utilized to manufacture the device described herein. System 900 comprises digital image capture apparatus 901. Digital image capture apparatus 900 is utilized to capture a plurality of three dimensional digital image pairs of a surface of a subject.

The three dimensional digital image pairs are provided to processor 903. The three dimensional digital image pairs are stored in data memory 905. Program memory 907 comprising various programs for processing three dimensional digital image pairs. A data file memory 909 stores processed three dimensional digital surface image pairs. A database 911 is utilized to store a library of processed three dimensional digital image data files. It will be appreciated by those skilled in the art that although data memory 905, program memory 907, data file memory 909 and data base 911, although shown as separate memories in FIG. 9, may comprise portions of one or more physical memories.

Associated with processor 903 is an input output interface 913. Input/output interface 13 comprises a display 915 and an input interface 917. Display 915 may be any one of a number of conventional displays, and input interface 917 may be any one or more of a number of conventional input apparatus. Display 915 may be a "touch screen" having an integrated input interface.

Processor 903, utilizing a program from program memory 907 is utilized to process each digital surface image pair to generate a three dimensional digital image surface portion of a subject's head. Display 915 may be utilized to display three dimensional digital image surface portions produced from each three dimensional digital image pair. Each surface is a surface portion image of a subject's head captured from a different vantage point. The corresponding data file for each three dimensional digital image surface portion is stored in data memory 905.

Each digital surface image portion is cleaned by removing extraneous data. The cleaning operation may be done via selection of extraneous portions by a system operator viewing each three dimensional digital image surface portion on display 915 and utilizing input apparatus 913 to select the data portion to be deleted by processor 903. In other embodiments, processor 903 may be programmed to either automatically delete extraneous portions or may be operated semi-automatically in combination with manual selection by a system operator.

Each three dimensional digital image surface portion is cropped such that only the portion of the head that is of interest is retained.

Each cleaned and cropped three dimensional digital image surface portion is then aligned and registered.

In alternate embodiments best-fit algorithms may be utilized to provide registration and alignment.

After all the digital surface image portions are registered and aligned the digital surface image portions are stitched or fused together to form a single three dimensional surface image of the entire surface of the subject's head or at least that portion of the head that is of interest. The resulting data file of the single three dimensional digital surface image is stored in data file 909 and may also be stored in data base 911.

In other embodiments different alignment and registration techniques may be employed including surface matching least squared, registration by identification and selection of key landmarks, or other mathematical approaches.

The portion of the head that comprises the portion of interest is identified. In one embodiment, the identification of the portion of interest is accomplished from a display of the portion of the head that is of interest and identification of that portion by a system operator and selecting that portion of the three dimensional surface image and its corresponding data file 909 for manufacture of a device or cranial plate.

System 900 may then be utilized to manufacture the device or cranial plate. More specifically, system 900 may further include manufacturing apparatus operable to utilize data file 909 to manufacture the device or cranial plate.

System 900 comprises a three dimensional printer 919. System 900 provides data file 909 to three dimensional printer 919. Three dimensional printer 919 utilizes data file 909 to print the device or cranial plate in plastic material.

Figure 10:
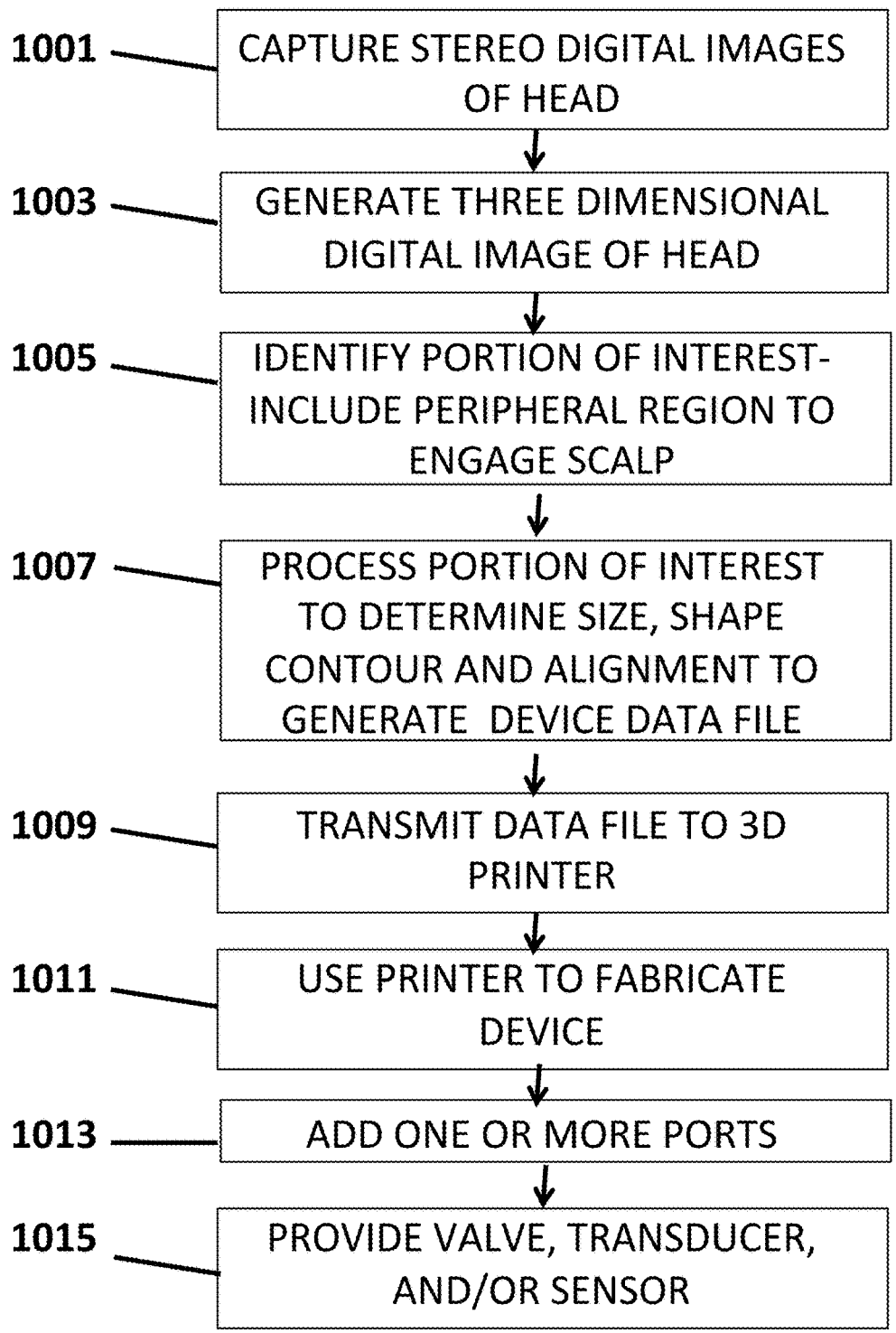
FIG. 10 illustrates steps in a first method.

The steps for one embodiment of a method of manufacturing a custom device for external application to the head of a patient over a removed portion of the cranium of the patient is shown in FIG. 10. At step 1001 stereographic digital image pairs are captured for the head of a subject by digital image pair capture apparatus 901 shown in FIG. 1. At step 1003, a three dimensional digital image of the surface of the head is generated from the stereographic digital image pairs. At step 1005, a portion of interest of the external surface of the head is identified. Where the custom device is a cranial plate, the portion of interest comprises at least the removed cranial portion and a portion extending around the periphery of the removed cranial portion. At step 1007, processor 903 determines one or more of a size, shape, contour and alignment for the custom device and generates a device data file. At step 1009, processor 903 transmits the data file to manufacturing apparatus such as three dimensional printer 919. At step 1011, three dimensional printer 919 utilizes the data file received from processor 903 to fabricate the custom device. At step 1013, the custom device is fabricated to include one or more ports. The formation of the ports may be done as part of the device fabrication step or may be a separate step in which the ports are drilled into the custom device. At step 1015, one or more of a valve, sensor, or transducer is provided in the one or more ports.

Figure 11:
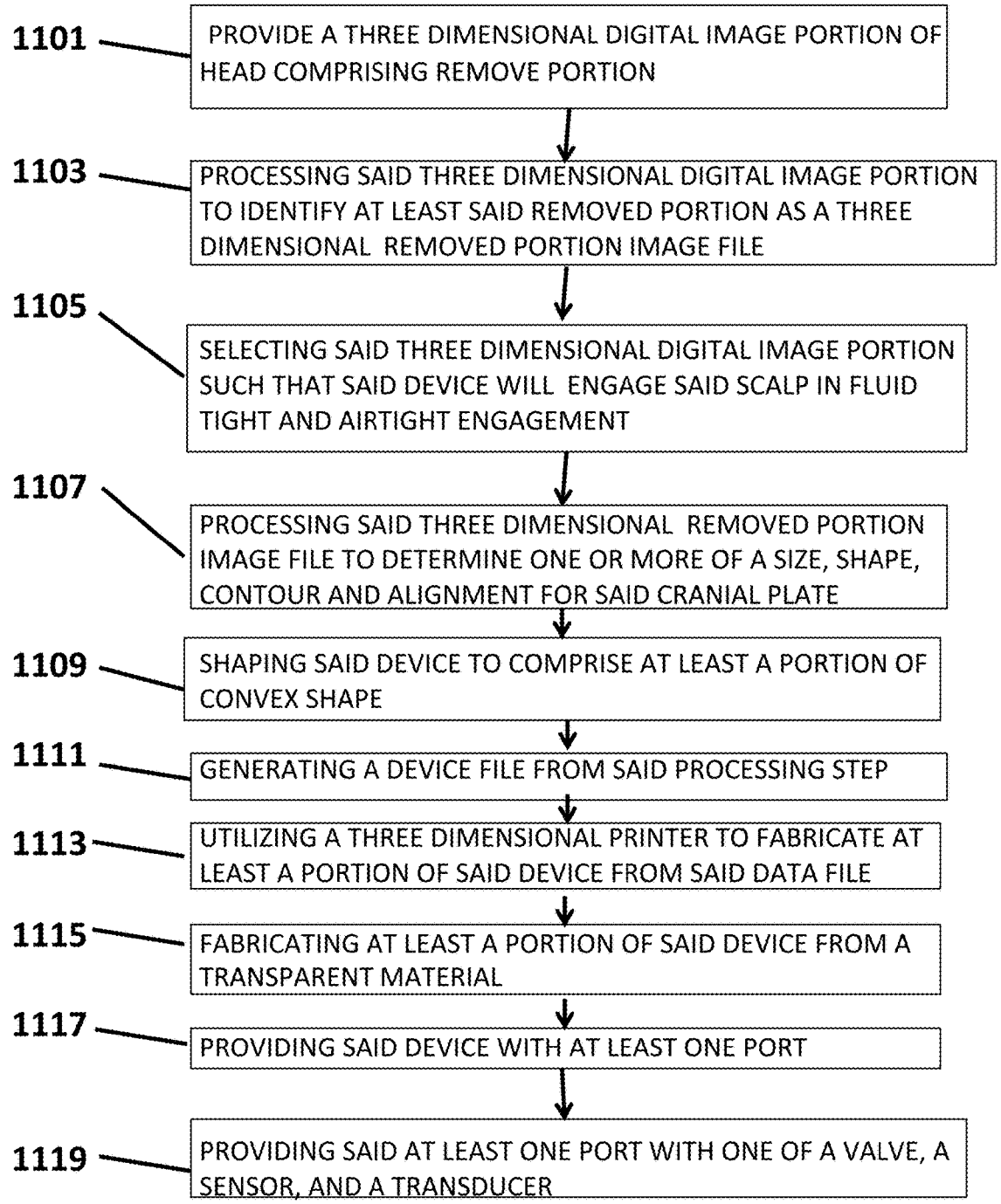
FIG. 11 illustrates steps in a second method.

Another embodiment of the invention directed to a method of manufacturing a device for external application to the scalp of a patient over a removed portion of the cranium of the patient is shown in FIG. 11. At step 1101, a three dimensional digital image portion of the head of the patient comprising at the removed portion is provided to processor 903. At step 1103, processor 903 is utilized to process the three dimensional digital image portion to identify at least the removed portion as a three dimensional removed portion digital image file. At step 1105, processor 903 selects the three dimensional removed portion digital image file to include a peripheral portion such that the device will engage the scalp in fluid tight and airtight engagement. At step 1107, processor 903 determines one or more of the size, shape, contour, and alignment of the device. At step 1109, processor 903 shapes the device to comprise at least a portion that is of convex shape. At step 1111, processor 903 generates a device data file. At step 1113, processor 903 transmits the device data file to three dimensional printer 919 and three dimensional printer 919 is utilized to fabricate at least a portion of the device. In various embodiments, the device may be fabricated from a plurality of pieces or portions, at least one portion is fabricated from a transparent material as indicated at step 1115. At step 1117, the device is provided with at least one port and at step 1119, the at least one port is provided with one of a valve, a sensor, and a transducer.

Figure 12:
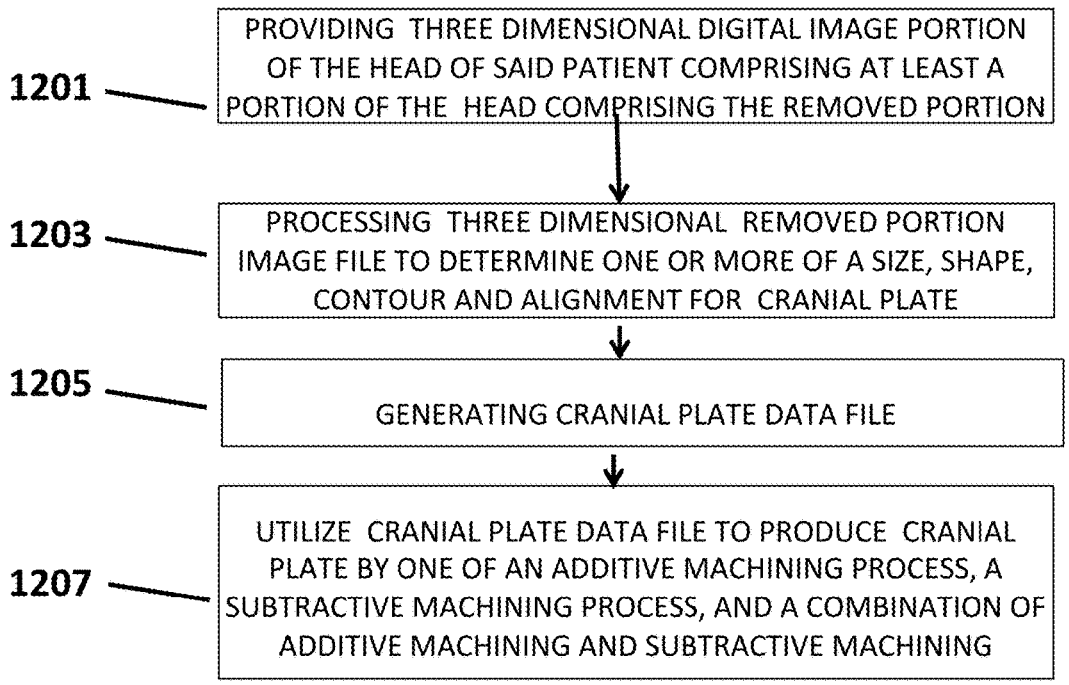
FIG. 12 illustrates steps in a third method.

FIG. 12 illustrates the steps in another embodiment of a method for manufacturing a cranial plate. At step 1201, processor 903 is provided with a three dimensional digital image portion of a patient's head. The three dimensional digital image portion comprises at least that portion of the head including the removed cranium. At step 1203, processor 903 processes the three dimensional digital image portion to determine one or more of a size, shape, contour and alignment for the cranial plate. At step 1205, processor 903 generates a cranial plate data file, and at step 1207 the cranial plate data file is utilized to produce a cranial plate by one of an additive machining or fabrication process, a subtractive machining process, and a combination of an additive machining or fabrication process and subtractive machining or fabrication process.

Figure 13:
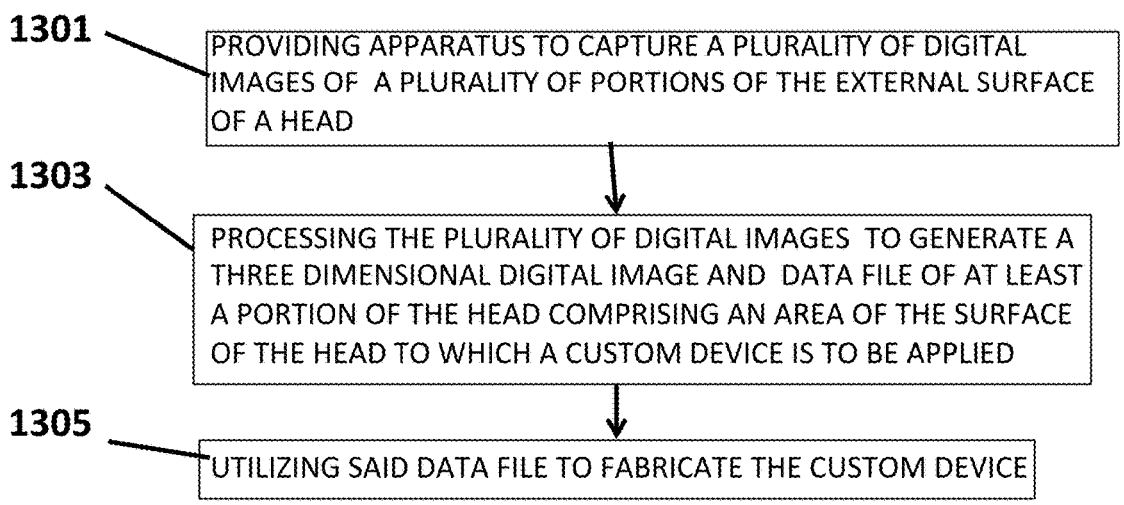
FIG. 13 illustrates steps in a fourth method.

FIG. 13 illustrates a method in which at step 1301, digital image capture apparatus 901 is provided to capture a plurality of digital images of a plurality of portions of the external surface of a head. At step 1303 processor 903 provides processing of the plurality of digital images to generate a three dimensional digital image and data file of at least a portion of the head comprising an area of the surface of the head to which a custom device is to be applied. At step 1305, system 900 utilizes the data file to fabricate the custom device.

Figure 14:
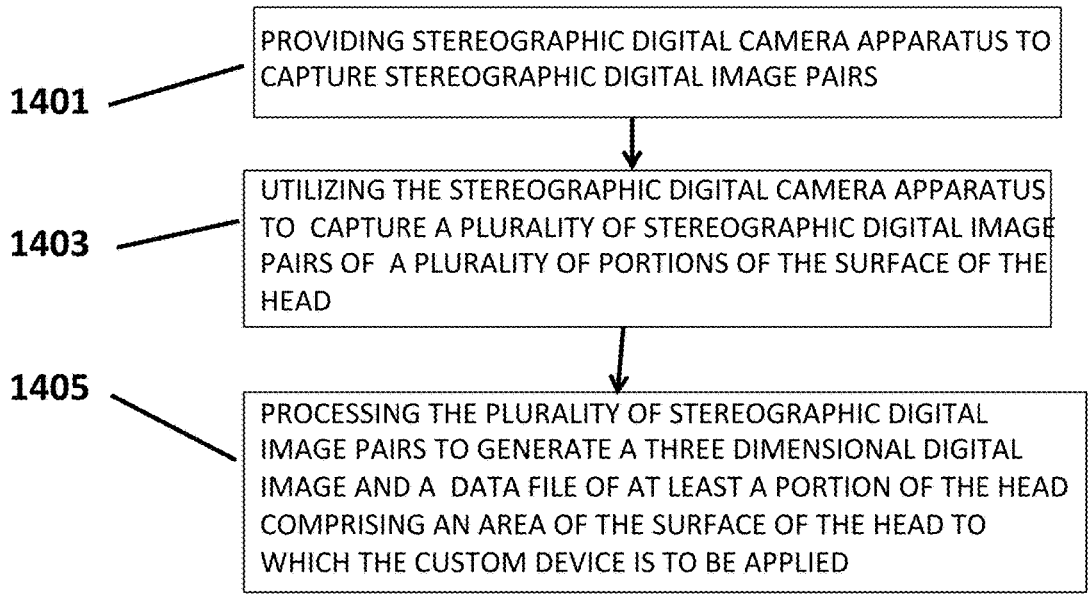
FIG. 14 illustrates steps in a sixth method.

In FIG. 14, a method for manufacturing a custom device is described. At step 1401, stereographic digital camera apparatus is provided to capture stereographic digital image pairs. At step 1403 the stereographic digital camera apparatus is utilized to capture a plurality of stereographic digital image pairs of a plurality of portions of the surface of the head. At step 1405, system 300 processes the plurality of stereographic digital image pairs to generate a three dimensional digital image and a data file of at least the portion of the head comprising the area of the surface to which the custom device is to be applied.

Figure 15:
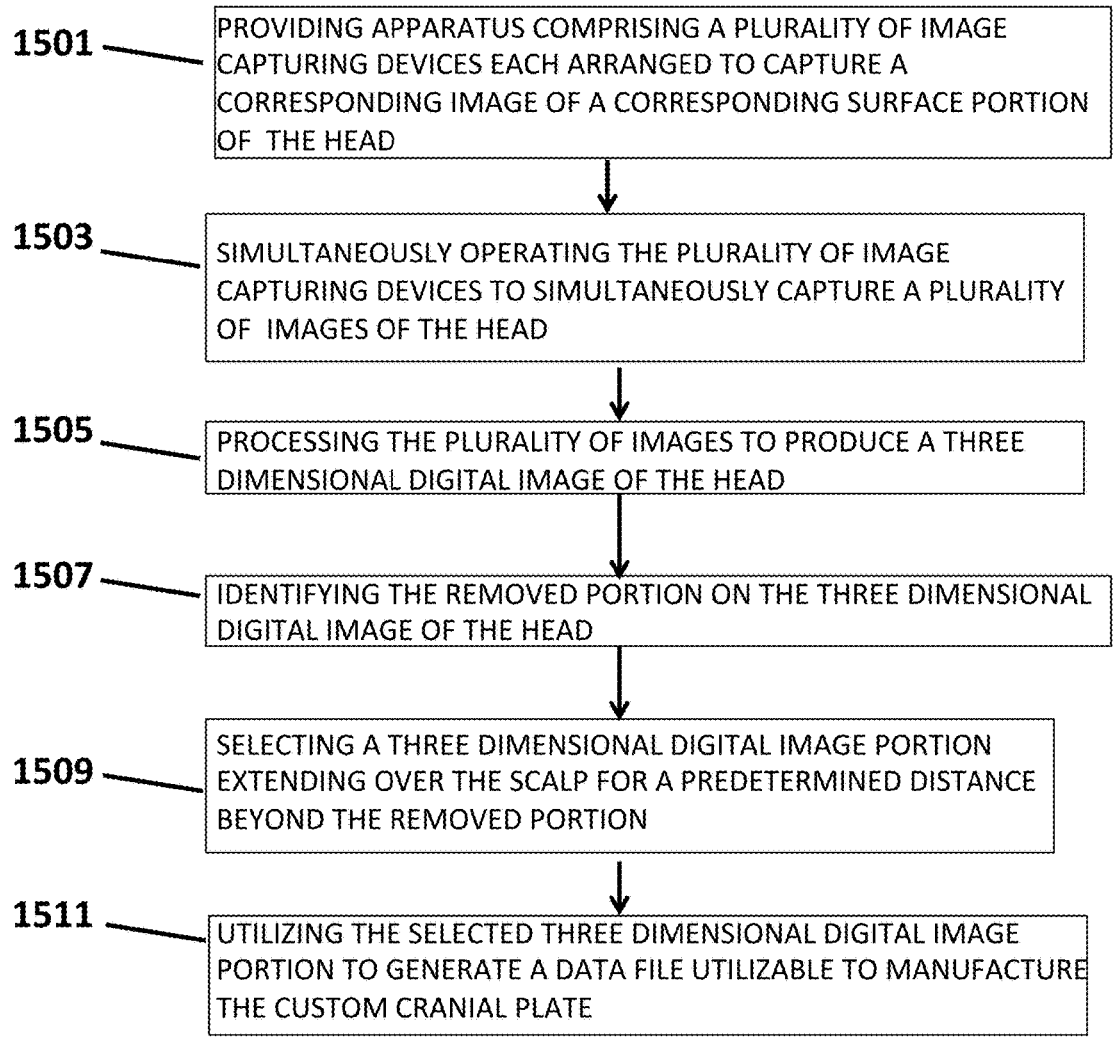
FIG. 15 illustrates steps in a seventh method.

In FIG. 15 an embodiment of a method of manufacturing a custom cranial plate for external application to the scalp of a patient over a removed portion of the cranium of the patient is shown. At step 1501, apparatus 901 is provided comprising a plurality of image capturing devices each arranged to capture a corresponding image of a corresponding surface portion of the head. At step 1503 the plurality of image capturing devices are operated to simultaneously capture a plurality of images of the head. At step 1505, processor 903 processes the plurality of images to produce a three dimensional digital image of the head. At step 1507, processor 903 is utilized to identify the removed portion on the three dimensional digital image of the head. At step 1509, processor 903 is utilized to select a three dimensional digital image portion extending over the scalp for a predetermined distance beyond the removed portion. At step 1511, system 300 utilizes the selected three dimensional digital image portion to generate a data file utilizable to manufacture the custom cranial plate.

Figure 16:
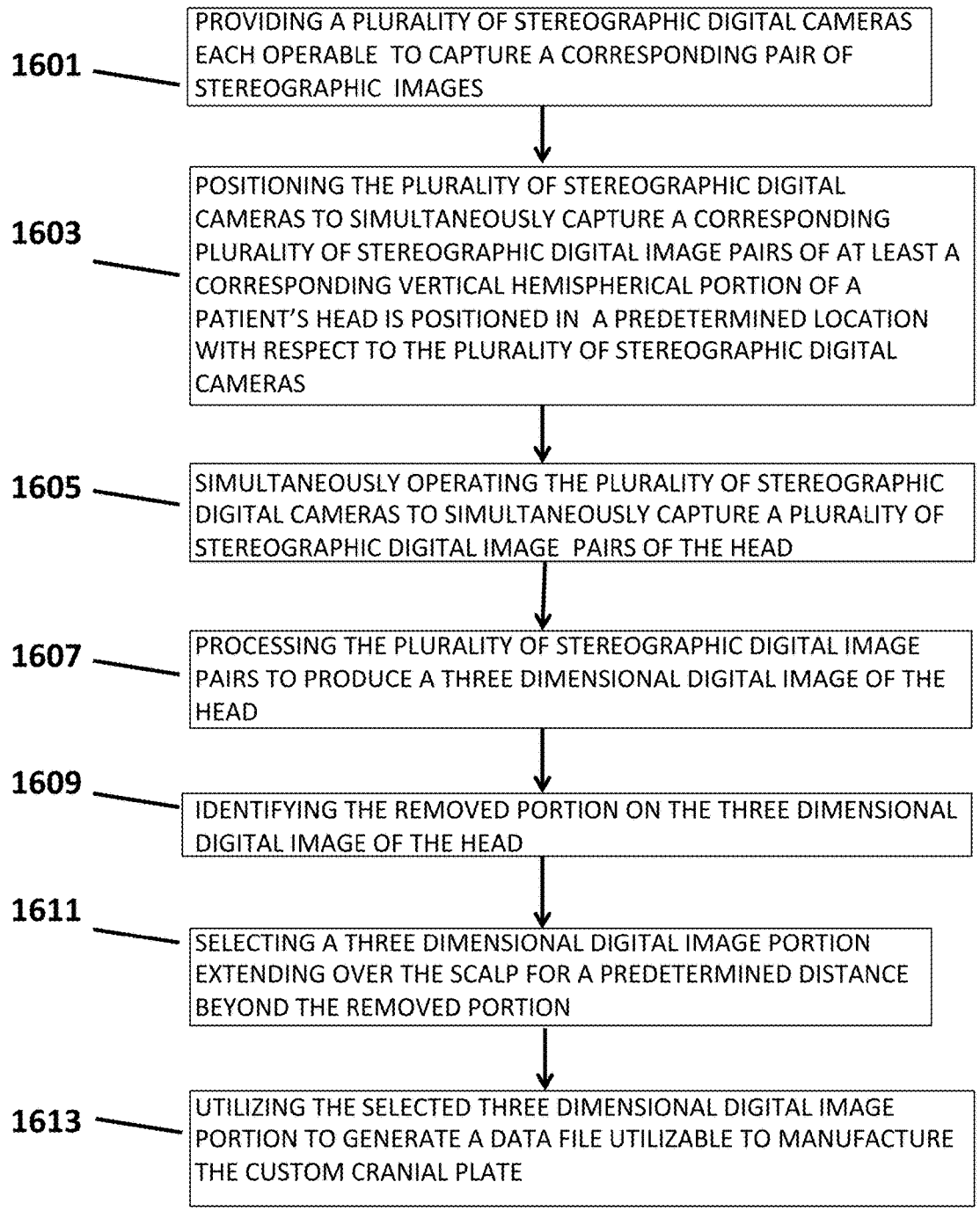
FIG. 16 illustrates steps in a eighth method.

FIG. 16 illustrates a method of manufacturing a custom cranial plate for external application to the scalp of a patient over a removed portion of the cranium of the patient. At step 1601 a plurality of stereographic digital cameras each operable to capture a corresponding pair of stereographic images is provided. The plurality of stereographic digital cameras is represented in FIG. 9 by digital image capture apparatus 901. At step 1603, the plurality of stereographic digital cameras are positioned to simultaneously capture a corresponding plurality of stereographic digital image pairs of at least a corresponding vertical hemispherical portion of the head when the patient is positioned in a predetermined location with respect to the plurality of stereographic digital cameras. At step 1605, the plurality of stereographic digital cameras are operated simultaneously to simultaneously capture a plurality of stereographic digital image pairs of the head. At step 1607, processor 903 processes the plurality of stereographic digital image pairs to produce a three dimensional digital image of the head. At step 1609, processor 903 is utilized to identify the removed portion on the three dimensional digital image of the head. At step 1611, processor 903 is utilized to select a three dimensional digital image portion extending over the scalp for a predetermined distance beyond the removed portion. At step 1613, system 900 utilizes the selected three dimensional digital image portion to generate a data file utilizable to manufacture the custom cranial plate.

Figure 17:
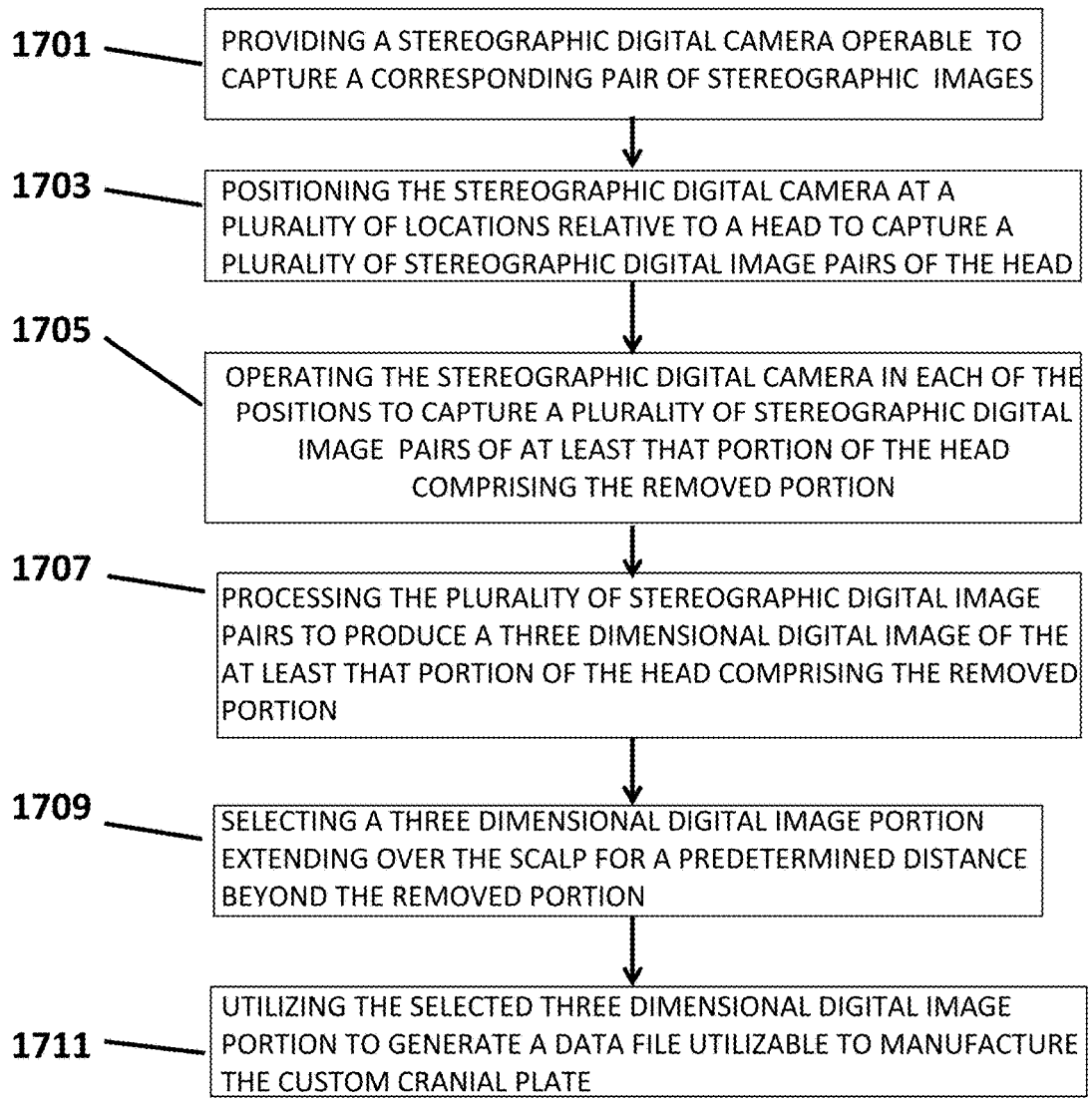
FIG. 17 illustrates steps in a ninth method.

FIG. 17 illustrates a method of manufacturing a custom cranial plate for external application to the scalp of a patient over a removed portion of the cranium of the patient. At step 1701 a stereographic digital camera operable to capture a corresponding pair of stereographic images is provided. The stereographic digital camera is represented in FIG. 9 by digital image capture apparatus 901. At step 1703, the stereographic digital camera is positioned at a plurality of locations relative to the head to thereby capture a plurality of stereographic digital image pairs of the head. At step 1705, the stereographic digital camera is operated in each of the positions to capture a plurality of stereographic digital image pairs of at least that portion of the head comprising the removed portion. At step 1707, system 300 processes the plurality of stereographic digital image pairs to produce a three dimensional digital image of the at least that portion of the head comprising the removed portion. At step 1709, a three dimensional digital image portion extending over the scalp for a predetermined distance beyond the removed portion is selected utilizing processor 903. At step 1711, processor 903 utilizes the selected three dimensional digital image portion to generate a data file utilizable to manufacture the custom cranial plate.

Figure 18:
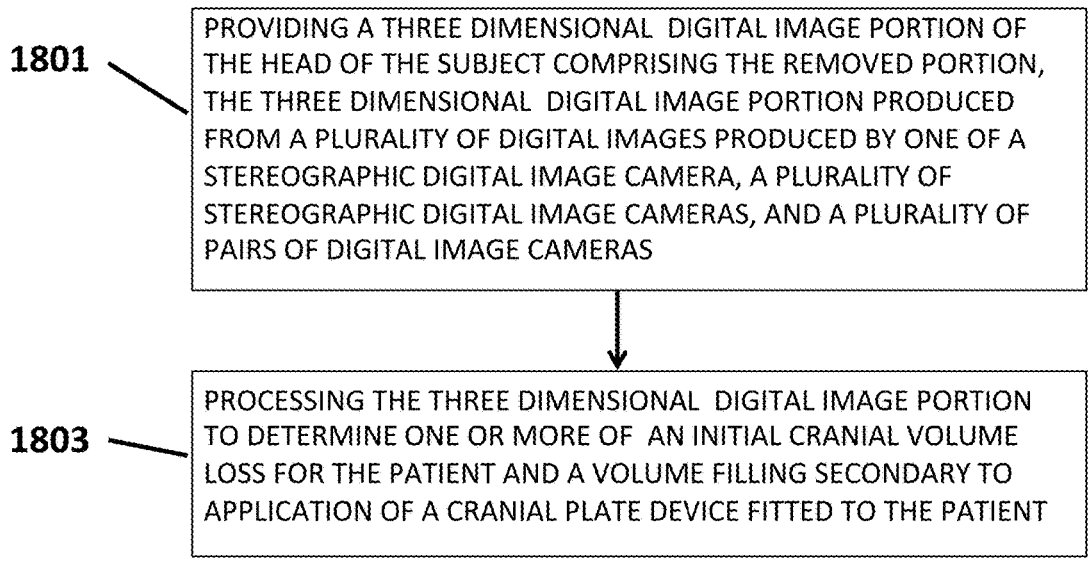
FIG. 18, which is on the same drawing sheet as FIG. 14, illustrates steps in a fifth method.

In various embodiments, a method for use with a subject having a removed cranium portion is shown in FIG. 18. At step 1801, a three dimensional digital image portion of the head of the subject comprising the removed portion is provided. The three dimensional digital image portion is produced from a plurality of digital images produced by one of a stereographic digital image camera, a plurality of stereographic digital image cameras, and a plurality of pairs of digital image cameras. At step 1803, the three dimensional digital image portion is processed by system 300 to determine one or more of an initial cranial volume loss for the patient and a volume filling secondary to application of a cranial plate device fitted to the patient.

It will be appreciated by those skilled in the art that although the embodiment shown utilizes a three dimensional printer, other manufacturing apparatus may be utilized, including, but not limited to, subtractive type machining or fabrication apparatus.

It will be further understood by those skilled in the art that various changes and modifications may be made to the method and apparatus of the invention without departing from its spirit or scope. It is intended that the invention not be limited to the embodiments shown and described herein, but that the invention be given the broadest possible scope permissible by law and that the invention is to be limited in scope only by the claims appended hereto.

The invention claimed is:

1. A method of manufacturing a custom protective device configured to be removably and externally affixed to a peripheral scalp portion of a patient's head, said peripheral scalp portion overlying a depressed portion of said patient's head where a portion of the cranium of said patient has been removed, and said peripheral scalp portion defined by a portion of said scalp extending outward about the entire periphery of said depressed portion by a predetermined distance on said scalp surrounding said depressed portion, the method comprising:
   providing an apparatus to capture a plurality of digital images of a plurality of portions of the external surface of said head;
   processing said plurality of digital images to generate a three dimensional digital image of the external surface of said scalp of said patient's head, said three dimensional image representing at least said peripheral scalp portion and said depressed portion;
   processing said three dimensional digital image to identify said peripheral scalp portion and said depressed portion represented by said three dimensional digital image;
   generating a three dimensional digital image file of said identified peripheral scalp portion and depressed portion;
   processing said three dimensional digital image file to determine one or more of a size, a shape, a contour, and a positional alignment for said custom device with respect to said patient's head;
   generating a device data file from said processed three dimensional digital image file; and
   utilizing said device data file to fabricate said custom device for said patient, said custom device further configured to cover said peripheral scalp portion and said depressed portion upon said affixing until said removed cranium portion is replaced.

2. A method in accordance with claim 1, wherein:
   said processing of said three dimensional digital image file is conducted such that said custom device is further configured to engage said peripheral scalp portion in a fluid tight and airtight engagement.

3. A method in accordance with claim 1, wherein:
   at least a portion of said custom device is formed from a transparent material.

4. A method in accordance with claim 1, further comprising:
   providing said custom device with at least one port.

5. A method in accordance with claim 4, further comprising:
   providing said at least one port with one of a valve, a sensor, and a transducer.

6. A method in accordance with claim 1, wherein:
   said fabricating is conducted by a three dimensional printer using said device data file.

7. A method in accordance with claim 1, further comprising:
   providing said apparatus as a stereographic digital camera apparatus; and
   operating said stereographic digital camera apparatus to capture a plurality of stereographic digital image pairs of a plurality of portions of the external surface of said head as said plurality of digital images, wherein said processing of said plurality of digital images comprises processing said stereographic digital image pairs to generate said three dimensional digital image.

8. A method in accordance with claim 1, wherein:
said custom protective device is configured to protect the intracranial contents of said patient from atmospheric pressure.

9. A method in accordance with claim 1, wherein:
at least a portion of said custom protective device comprises a convex shape.

10. A method in accordance with claim 1, further comprising:
providing said apparatus as a plurality of image capturing devices each arranged to capture a corresponding one of said digital images of a corresponding surface portion of said head; and
operating said plurality of image capturing devices to simultaneously capture said plurality of digital images.

11. A method in accordance with claim 1, further comprising:
providing said apparatus as a plurality of stereographic digital cameras;
positioning said plurality of stereographic digital cameras in a manner capable of simultaneously capturing a corresponding plurality of stereographic digital image pairs of at least a corresponding vertical hemispherical portion of said head with said patient positioned in a predetermined location with respect to said plurality of stereographic digital cameras; and
simultaneously operating said plurality of stereographic digital cameras to simultaneously capture the plurality of stereographic digital image pairs of said head as said plurality of digital images.

12. A method in accordance with claim 1, further comprising:
providing said apparatus as a stereographic digital camera;
positioning said stereographic digital camera at a plurality of locations relative to said head; and
operating said stereographic digital camera in each of said locations to capture a plurality of stereographic digital image pairs of at least the portion of said head comprising said removed portion as said plurality of digital images,
wherein said processing of said plurality of digital images comprises processing said plurality of stereographic digital image pairs to produce said three dimensional digital image.

13. A method in accordance with claim 1, wherein:
said removed cranium portion is a bone flap.

14. A method in accordance with claim 1, wherein:
said custom device is a cranial plate.

15. A method in accordance with claim 1, wherein:
said custom device comprises optically transparent polycarbonate permitting observation of the depressed portion therethrough after said affixing.

16. A method in accordance with claim 1, wherein:
said fabricating is conducted by one of an additive machining process, a subtractive machining process, and a combination of additive and subtractive machining.

17. A method in accordance with claim 1, wherein:
said fabricating is conducted by thermoplastic forming.

* * * * *